United States Patent [19]
Day

[11] Patent Number: 6,071,396
[45] Date of Patent: Jun. 6, 2000

[54] GEL-MATRIX ELECTROPHORESIS

[75] Inventor: Ian Nicholas Monsarratt Day, Southampton, United Kingdom

[73] Assignee: University College London, London, United Kingdom

[21] Appl. No.: 08/849,697

[22] PCT Filed: Dec. 15, 1994

[86] PCT No.: PCT/GB94/02745

§ 371 Date: Aug. 15, 1997

§ 102(e) Date: Aug. 15, 1997

[87] PCT Pub. No.: WO96/18891

PCT Pub. Date: Jun. 20, 1996

[51] Int. Cl.[7] .................................................... G01N 27/26
[52] U.S. Cl. ............................................................ 204/616
[58] Field of Search ..................................... 204/456, 465, 204/466, 467, 606, 615, 616, 618, 619, 620

[56] References Cited

U.S. PATENT DOCUMENTS 3,930,983   1/1975   Sieber ...................................... 204/299

FOREIGN PATENT DOCUMENTS 2 671 631 A1   7/1992   France .

WO 93/00986   1/1993   WIPO .

OTHER PUBLICATIONS

Day et al., "Electrophoresis for Genotyping: Microtiter Array Diagonal Gel Electrophoresis on Horizontal Polyacrylamide Gels, Hydrolink, or Agarose", *Analytical Biochemistry,* 222:389–395 (1994), month unknown.

*Primary Examiner*—T. Tung
*Assistant Examiner*—Abe Noguerola
*Attorney, Agent, or Firm*—Marshall, O'Toole, Gerstein, Murray & Borun

[57] ABSTRACT

The invention provides an electrophoresis gel-matrix layer, usually adhered upon a support plate, having two mutually opposite ends for application of an electrophoresis voltage thereto, an exposed major surface extending between the two ends, and a plurality of wells in the thickness of the layer and open at the said exposed surface, wherein the wells are arranged in a plurality of rows each extending transversely of the end-to-end direction of the layer and the wells in successive rows are progressively offset in the transverse direction whereby electrophoresis tracks obtained from wells of one row will pass, if extended so far, between wells of at least one other row and tracks obtained therefrom. The invention also provides a method of making, and a method of using, such a gel-matrix layer.

12 Claims, 2 Drawing Sheets

GEL-MATRIX ELECTROPHORESIS

This application is a National Stage of International Application No. PCT/GB94/02745, filed Dec. 15, 1994.

FIELD OF THE INVENTION

This invention relates to electrophoresis, in particular the electrophoresis of numerous samples.

BACKGROUND OF THE INVENTION

Electrophoresis of, for example, samples of DNA fragments are commonly performed in a gel matrix of either agarose or acrylamide. In the case of agarose, the gel is usually poured while molten on to a horizontal glass plate on which it forms a layer which then sets; and in order to handle a plurality of samples simultaneously a "comb" having a row of protruding teeth or pegs is positioned so that the pegs project into the agarose layer while it sets. When the agarose layer has set, the comb is removed to leave a row of holes or wells in the layer adjacent one edge of the plate. These wells can then be loaded with samples which are then subjected simultaneously to electrophoresis by applying a voltage from end to end of the agarose layer so as to form a corresponding number of parallel electrophoresis tracks each extending from a respective one of the loaded wells towards the other end of the plate. In order to accommodate a larger number of samples than can conveniently be loaded into a single row of wells, the comb may be formed with a second row of pegs to form a second row of wells in the agarose, the second row being spaced from the first, and also from the other end of the plate, by a distance greater than the desired length of the electrophoresis tracks which are to be obtained.

In the case of an acrylamide gel layer, the open-faced preparation method used for agarose is not suitable, because acrylamide does not polymerise in the presence of air. It is therefore usual to prepare the acrylamide as a sandwich layer between two glass plates and, since neither major face of the layer is accessible, to form the wells in one end edge of the acrylamide layer. Electrophoresis is then carried out with the sandwich vertical, and its edge in which the wells are formed as its upper edge, so that samples can be loaded into the wells. It would not be practical in such a case to provide a spaced additional row of wells to enable a larger number of samples to be handled simultaneously. Acrylamide does, however, provide higher resolution of samples and, other considerations being equal, would be preferred to agarose.

There is a need for an electrophoresis gel-matrix layer which enables larger numbers of samples to be handled simultaneously than is possible with either of the known multiple-well plates described above, and it is an object of the invention to provide an improved electrophoresis gel-matrix layer which achieves this.

SUMMARY OF THE INVENTION

According to the invention there is provided an electrophoresis gel-matrix layer having two mutually opposite ends for application of an electrophoresis voltage thereto, an exposed major surface extending between the two ends, and a plurality of wells in the thickness of the layer and open at the said exposed surface, wherein the wells are arranged in a plurality of rows each extending transversely of the end-to-end direction of the layer and the wells in successive rows are progressively offset in the transverse direction whereby electrophoresis tracks obtained from wells of one row will pass, if extended so far, between wells of at least one other row and tracks obtained therefrom.

The invention also provides a method of making, and a method of using, such a gel-matrix layer.

Usually, the gel-matrix layer according to the invention will be adhered upon a support plate.

Usually also, the wells will be arranged in a regular lattice. In a preferred embodiment of the invention, the wells are arranged in a square lattice pattern of equispaced rows and columns, perpendicular to one another and both offset at an angle to the end-to-end direction of the matrix layer. If for example, the transverse rows of wells are at an angle of $\tan^{-1}3$ (about 71½°) to the end-to-end direction of the layer, or at 18½° to the ends of the layer, electrophoresis tracks originating at the wells of one row will pass between wells of the next two rows, before (if they extend so far) colliding with wells in the next row encountered.

The invention, and preferred embodiments of electrophoretic gel-matrix layers and plates in accordance with it, are disclosed in greater detail in the following description with reference to the accompanying drawings, immediately

DETAILED DESCRIPTION

Figure 1:
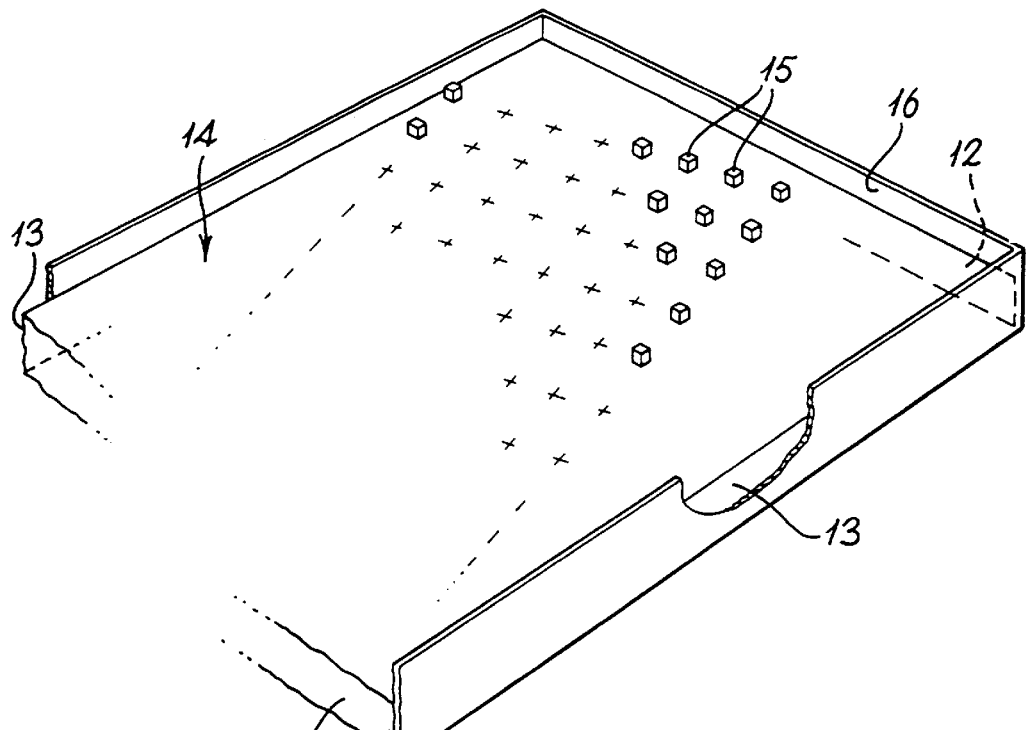
FIG. 1 is a perspective view of a toothed or pegged mould for casting a gel-matrix layer.
Figure 2:
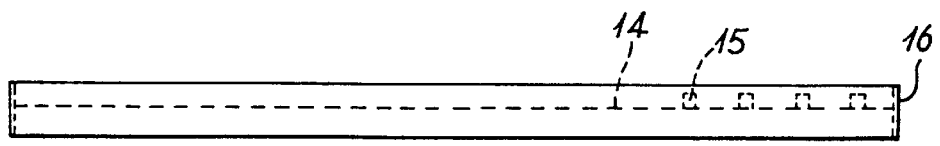
FIG. 2 is a side view of the mould shown in FIG. 1.

The mould shown in FIG. 1 comprises a rectangular base plate 11 having ends 12, sides 13 and a flat upper surface 14 from which project a plurality of pegs or teeth 15. The teeth 15 are disposed in a regular square lattice pattern, in rows and columns which are angularly offset relative to the ends 12, or the end-to-end direction, of the mould 11. As illustrated (and as will be seen more clearly from FIG. 4 referred to below) the rows of teeth 15, extending transversely across the surface 14 of the mould, are at an angle of $\tan^{-1}3$ (about 71½°) to the sides 13 or the end-to-end direction of the mould and thus at about 18½° to the ends 12.

Preferably, and as shown, there are twelve rows of teeth 15, with eight teeth in each row, and the centre-to-centre spacing of the teeth in both directions is 9 mm. Preferably also, each tooth is of square cross-section, with its side faces parallel to the ends 12 and sides 13 of the mould 11, with cross-sectional dimensions of 2 mm×2 mm and also a height of 2 mm. The plate 11 and teeth 15 may be formed integrally from a single block of, for example, Perspex, by machining away part of the thickness of the block (except where the teeth are left) so as to leave the teeth upstanding from the remainder of the thickness.

Round its perimeter, the mould 11 is provided with a rim 16 which is closely adherent to the ends 12 and sides 13 and projects upwardly from them by an amount, say 3 mm, which is greater than the height of the teeth 15.

Figure 3:
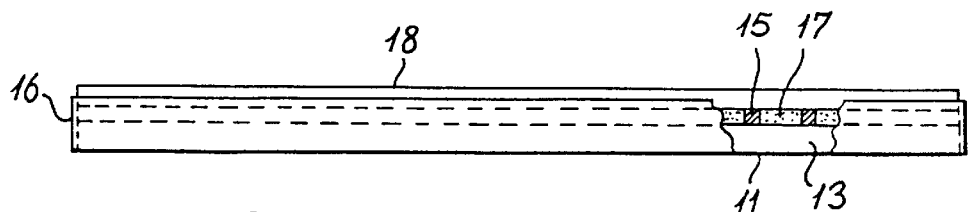
FIG. 3 is a view similar to that shown in FIG. 2, but partly broken away and showing a gel layer within the mould and a support plate laid over the gel layer.

In use of the mould 11 with acrylamide to form the gel layer, it is filled, to a depth at which the tops of the teeth 15 are just covered, with the acrylamide material 17 which is to polymerise to form the desired gel-matrix layer; and a cover plate 18, as shown in FIG. 3, is carefully laid on the material 17, progressively from one end to the other, to avoid entrapment of any air as bubbles between the material 17 and the plate 18, and is pressed down on to the teeth 15 so that no material 17 remains between the teeth 15 and the plate 18. Any excess of the material 17 is expelled over the rim 16, and the remaining material 17 is allowed to polymerise and to become firmly adherent to the plate 18. The acrylic material 17 is then polymerised to polyacrylamide, suitably by TEMED and ammonium persulphate. If the material 17 is acrylamide, that surface of the plate 18 to which it is to adhere is preferably pretreated by silanising with a silanising agent which may suitably be 0.5% gamma-methacryloxypropyltrimethooxysilane/0.5% glacial acetic acid/ethanol v/v, as obtainable from Sigma Chemicals.

If the layer 17 is to be of agarose gel, it is poured in at a temperature at which it is suitably liquid, but spacers (not illustrated) are first laid on the surface 14 to prevent the plate 18 from resting on the teeth 15 and to ensure that agarose material remains in the gaps between the teeth and the plate 18.

Figure 4:
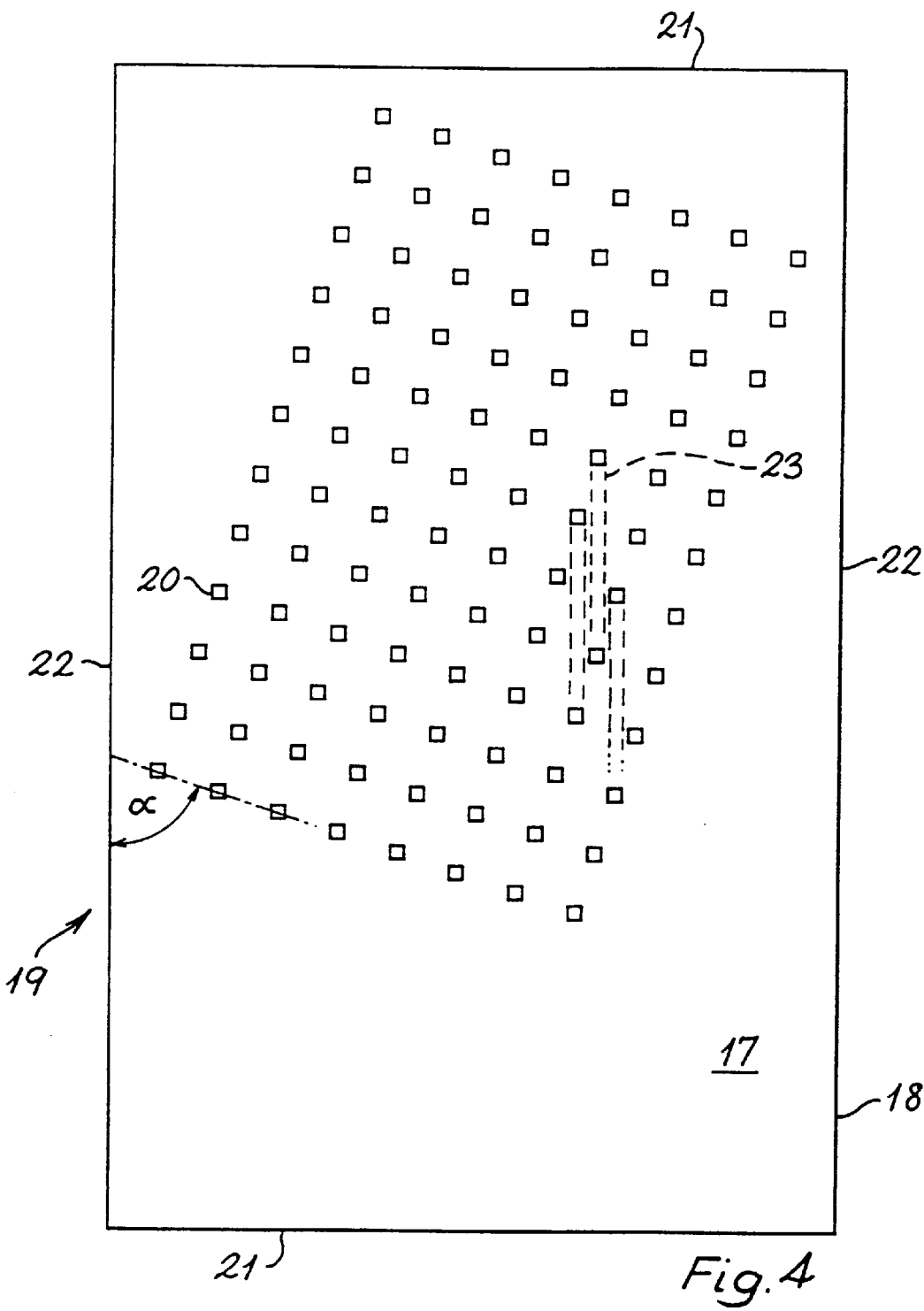
FIG. 4 is a plan view of the gel layer after it and its support plate have been removed from the mould.
Figure 5:
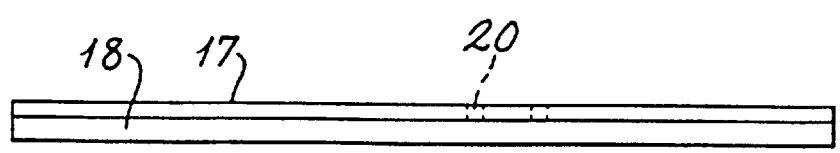
FIG. 5 is an end view of the gel layer shown in FIG. 4 and of its support plate.

When the material 17 has polymerised or set and is firmly adhered to the plate 18, both are removed, together, from the mould. This can be achieved by carefully prising one end of the plate 18 away from the surface 14 of the mould, when the polymerised gel-matrix layer 17 remains adherent to the plate 18 and peels away from the mould surface 14 and teeth 15. The resulting gel-matrix electrophoresis plate 19, consisting of the layer 17 and the support plate 18 to which it is adhered, is shown in FIGS. 4 and 5. Formed in the gel layer 17 are wells 20, complementary to the teeth 15. If the layer 17 is acrylamide, the plate 18 forms the bottom of the wells 20, and the bond between the gel layer and the plate at their interface is effective to prevent sample leakage along the interface from the bottoms of the wells. If the gel layer is of agarose, where the interface bonding would be less effective to prevent leakage, the bottoms of the wells are formed by the agarose which was left between the plate 18 and the teeth 15 by providing the above-mentioned spacers for the plate 18. The wells 20, like the teeth 15, are arranged on a square lattice of twelve rows, each of eight wells, with the rows, extending transversely across the width of the plate 19, disposed at an angle $\alpha$ to the lengthwise direction of the plate. As illustrated, though only by way of example, the angle $\alpha$ is such that $\tan\alpha = 3$. This means that when a sample loaded into a well 20 is subjected to electrophoresis by applying a voltage between ends 21 of the layer 17 so as to provide in the layer 17 an electric field in the end-to-end direction parallel to sides 22 of the plate, the resulting electrophoresis track 23, extending in the lengthwise direction parallel to the sides 22, can pass between wells of the next two rows of wells without interfering either with them or with tracks originating with them, before encountering one of the wells in the third row.

It will be seen that this embodiment of the invention, and the invention generally, provides a remarkably compact arrangement of wells and a correspondingly efficient use of the available gel. Furthermore, the particular arrangement shown in FIG. 4, namely the arrangement of the wells 20 in a 12×8 square lattice pattern with 9 mm centre-to-centre spacing, is the same as that of the wells of a standard microtitre plate. It will very often be the case that the samples which are to be analysed or examined by electrophoresis will have been produced, in large numbers, in standard microtitre plates; and the use of an electrophoresis plate like that in FIG. 4, with its wells arranged in the identical manner, can lead to great economies of time and labour since the transfer of samples from the wells of a microtitre plate to the wells of the electrophoresis plate can be performed automatically or semi-automatically by the use of a multichannel pipette.

It is with this use of multichannel pipettes, possibly robotically operated, in mind that the wells 20 are preferably made not much smaller than 2 mm×2 mm, which allows for some misalignment of individual pipette tips. As stated above, with wells of these dimensions in a 9 mm×9 mm lattice it is permissible to choose an angular offset such that $\alpha = \tan^{-1} 3$. If an even more compact arrangement were required, in which (still with the 9 mm×9 mm lattice spacing) the track 23 from a well in one row would pass through the next three rows without interference before encountering another well in the fourth row, thus requiring reduced angular offset such that $\tan\alpha = 4$, it would probably be advisable to reduce the transverse dimension of the tracks 23, and thus of the wells 20, from 2 mm to about 1.5 mm. The maximum track length when $\tan\alpha = 3$ is about 28 mm, which is adequate, when using polyacrylamide as the gel layer 17, for many pattern recognition analyses which depend on mobility differences greater than 5–10%. Increasing a to a value such that $\tan a = 4$ gives an increased available track length of about 35 mm.

A further advantage of arranging the wells 20 identically with those of a standard microtitre plate is that the same standard microtitre grid transparency which has been marked up to identify the samples in the wells of a microtitre plate can also be used to identify the tracks 23 obtained from those samples after they have been transferred to the corresponding wells an electrophoresis plate 19. After electrophoresis and any necessary staining or other procedure to reveal the tracks 23, the marked-up microtitre grid transparency is used as an overlay on the plate 19 while it is photographed, to provide a record identifying the tracks with maximum simplicity and minimum expenditure of time on the necessary record keeping.

As shown in FIG. 4, the plate 19 has a well-free region at its lower end, to accommodate tracks 23 from the adjacent wells 20. A similar plate, if it also has a well-free region to one side of its array of wells 20, may be re-used by turning it. through 90°, i.e. by subjecting it to an electrophoresis voltage inducing a field from side to side of the plate as viewed in FIG. 4. The tracks resulting from the second use will be at right angles to the tracks 23 from the first use, and can readily be distinguished and read without confusion.

What is claimed is:

1. An electrophoresis gel-matrix layer having two mutually opposite ends for application of an electrophoresis voltage thereto, an exposed major surface extending between the two ends, and a plurality of wells in the thickness of the layer and open at the said exposed surface, wherein the wells are arranged in a plurality of rows each extending transversely of the end-to-end direction of the layer and the wells in successive rows are progressively offset in the transverse direction whereby electrophoresis tracks obtained from wells of one row will pass, if extended so far, between wells of at least one other row and tracks obtained therefrom.

2. A gel-matrix layer as claimed in claim 1, wherein the wells are arranged in a regular lattice pattern.

3. A gel-matrix layer as claimed in claim 2, wherein the wells are arranged in a square lattice pattern of equispaced transverse rows and columns which are perpendicular to the rows, and the rows and columns are angularly offset at respective angles relative to the end-to-end direction of the matrix layer.

4. A gel-matrix layer as claimed in claim 3, wherein the rows of wells are disposed at an angle of about $\tan^{-1}3$ to the end-to-end direction of the layer.

5. A gel-matrix layer as claimed in claim 3, wherein the rows of wells are disposed at an angle of about $\tan^{-1}4$ to the end-to-end section of the layer.

6. A gel-matrix layer as claimed in claim 1, supported by and adhered upon a support plate.

7. A gel-matrix layer adhered to a support plate, as claimed in claim 6, wherein the gel-matrix layer is of agarose.

8. A gel-matrix layer adhered to a support plate, as claimed in claim 6, wherein the gel-matrix layer is of polyacrylamide.

9. A method of making an electrophoresis gel-matrix layer adhered upon a support plate, comprising the steps of:

providing a rectangular mould tray having a horizontally disposed flat surface bounded by upstanding side walls and end walls and having a plurality of pegs or teeth projecting upwardly from the flat surface, introducing gel-forming material in flowable condition into the mould to a depth at which it covers the pegs or teeth, laying a support plate on the gel-forming material in the mould, in contact with the exposed free surface of said material, allowing the gel-forming material to gel and adhere to the support plate, and removing the support layer, and the gel layer adhered thereto, together from the mould and the pegs or teeth thereof, wherein the pegs or teeth are arranged in a plurality of rows each extending across the said flat surface of the mould transversely of the end-to-end direction of the said flat surface, with the pegs or teeth in successive rows being progressively offset in the transverse direction.

10. A method as claimed in claim 9, wherein the pegs or teeth of the mould are arranged in a regular lattice pattern.

11. A method of effecting simultaneous electrophoresis of multiple samples, comprising the steps of placing each sample in a respective one of a plurality of wells arranged in a lattice pattern of rows and columns in a layer of gel material, and subjecting all the samples to electrophoresis by applying a voltage in a direction, along the layer of gel material, which is at an angle to the rows of wells such that an electrophoresis track extending in that direction from a well in one of said rows will pass between wells in at least one adjacent row before encountering, if sufficiently extended, a well in a more remote row.

12. A method as claimed in claim 11 and including the preliminary step of removing the samples, simultaneously, each from a respective one of a plurality of wells of a microtitre plate, prior to placing the samples simultaneously in the wells in the layer of gel material, the wells of the microtitre plate being arranged in the same lattice pattern of rows and columns as that of the wells of the layer of gel material.

* * * * *